US010357435B2

(12) United States Patent
Lee

(10) Patent No.: US 10,357,435 B2
(45) Date of Patent: *Jul. 23, 2019

(54) PHOTO-CURABLE RESIN COMPOSITIONS AND METHOD OF USING THE SAME IN THREE-DIMENSIONAL PRINTING FOR MANUFACTURING ARTIFICIAL TEETH AND DENTURE BASE

(71) Applicant: DENTCA, Inc., Los Angeles, CA (US)

(72) Inventor: Jae Sik Lee, Los Angeles, CA (US)

(73) Assignee: DENTCA, INC., Torrance, CA (US)

( * ) Notice: Subject to any disclaimer, the term of this patent is extended or adjusted under 35 U.S.C. 154(b) by 514 days.

This patent is subject to a terminal disclaimer.

(21) Appl. No.: 14/262,495

(22) Filed: Apr. 25, 2014

(65) Prior Publication Data

US 2014/0239527 A1    Aug. 28, 2014

Related U.S. Application Data

(63) Continuation-in-part of application No. 13/865,907, filed on Apr. 18, 2013, now Pat. No. 9,456,963.

(60) Provisional application No. 61/738,970, filed on Dec. 18, 2012, provisional application No. 61/926,834, filed on Jan. 13, 2014.

(51) Int. Cl.
| | | |
|---|---|---|
| *A61K 6/08* | (2006.01) | |
| *B33Y 70/00* | (2015.01) | |
| *A61K 6/083* | (2006.01) | |
| *A61C 13/00* | (2006.01) | |
| *B29C 64/106* | (2017.01) | |

(52) U.S. Cl.
CPC .......... *A61K 6/083* (2013.01); *A61C 13/0013* (2013.01); *B29C 64/106* (2017.08); *B33Y 70/00* (2014.12)

(58) Field of Classification Search
CPC .... A61K 6/083; A61C 13/0013; B33Y 70/00; B29C 64/106
USPC ............................................. 522/92, 100, 90
See application file for complete search history.

(56) References Cited

U.S. PATENT DOCUMENTS

| | | | | |
|---|---|---|---|---|
| 4,945,032 A * | 7/1990 | Murphy | ............. | B29C 67/0066 264/1.38 |
| 6,025,114 A * | 2/2000 | Popat | ............. | G03F 7/0037 264/401 |
| 6,242,505 B1 * | 6/2001 | Gassner | ............. | B44C 1/20 522/18 |
| 6,821,462 B2 | 11/2004 | Schulman et al. | | |
| 7,232,646 B2 * | 6/2007 | Klare | ............. | B29C 67/0055 430/284.1 |
| 7,514,477 B2 * | 4/2009 | Klare | ............. | A61L 27/26 264/401 |
| 7,763,669 B2 * | 7/2010 | Klare | ............. | C08G 18/672 522/121 |
| 8,263,651 B2 * | 9/2012 | Hammock | ............. | A61K 31/17 514/475 |
| 2002/0033548 A1 | 3/2002 | Brodkin et al. | | |
| 2003/0060534 A1 * | 3/2003 | Fukushima | ............. | C08K 5/0025 523/115 |
| 2007/0049656 A1 | 3/2007 | Jia et al. | | |
| 2008/0287564 A1 | 11/2008 | Klare et al. | | |
| 2010/0016464 A1 | 1/2010 | Craig et al. | | |
| 2011/0049738 A1 | 3/2011 | Sun et al. | | |
| 2011/0275035 A1 | 11/2011 | Lu | | |
| 2012/0093741 A1 | 4/2012 | Maletz et al. | | |
| 2012/0196249 A1 | 8/2012 | Maletz et al. | | |
| 2012/0309864 A1 | 12/2012 | Ruppert et al. | | |
| 2014/0131908 A1 * | 5/2014 | Sun | ............. | A61K 6/083 264/16 |

FOREIGN PATENT DOCUMENTS

| | | |
|---|---|---|
| CN | 102688106 | 9/2012 |
| JP | S61152715 | 7/1986 |
| JP | H08311115 | 11/1996 |
| JP | 2002029912 | 1/2002 |
| JP | 2007126417 | 5/2007 |
| KR | 1020050083646 | 8/2005 |

OTHER PUBLICATIONS

United States Patent and Trademark Office U.S. Appl. No. 13/865,907, Office Action dated Aug. 3, 2015, 22 pages.
United States Patent and Trademark Office U.S. Appl. No. 13/865,907, Office Action dated Feb. 1, 2016, 21 pages.
Froes-Salgado et al. Influence of the Base and Diluent Methacrylate Monomers on the Polymerization Stress and its Determinants, Sep. 1, 2011, Journal of Applied Polymer Science, vol. 123, 2985-2991, 7 pages.
PCT International Application No. PCT/US2013/037218, Notification of Transmittal of the International Search Report and the Written Opinion of the International Searching Authority, or Declaration dated Sep. 4, 2013, 14 pages.
PCT International Application No. PCT/US2014/036975, Written Opinion of the International Searching Authority dated Sep. 5, 2014, 13 pages.
The State Intellectual Property Office of the People's Republic of China Application No. 201480029858.9, Office Action dated Aug. 19, 2016, 23 pages.
Japan Patent Office Application Serial No. 2016-509156, Office Action dated Mar. 28, 2017, 3 pages.
Korean Intellectual Property Office Application No. 10-2015-7032508, Notice of Allowance dated Oct. 26, 2017, 2 pages.

\* cited by examiner

*Primary Examiner* — Sanza L. McClendon
(74) *Attorney, Agent, or Firm* — Lee, Hong, Degerman, Kang & Waimey

(57) ABSTRACT

A composition includes a light-curable viscous mixture that includes: 0-50% by weight of a poly(methyl methacrylate)/methyl methacrylate solution; 5-20% by weight of at least one kind of multifunctional aliphatic (meth)acrylate; 5-40% by weight of at least one kind of aliphatic urethane (meth) acrylate oligomer; 25-65% by weight of at least one kind of difunctional bisphenol-A dimethacrylate; 0.1 to 5% by weight of at least one kind of a photoinitiator; 0.05 to 2% by weight of at least one kind of light stabilizer; and 0.1 to 3% by weight of color pigment based on the total weight of the composition.

19 Claims, No Drawings

PHOTO-CURABLE RESIN COMPOSITIONS AND METHOD OF USING THE SAME IN THREE-DIMENSIONAL PRINTING FOR MANUFACTURING ARTIFICIAL TEETH AND DENTURE BASE

CROSS REFERENCE TO RELATED APPLICATIONS

Pursuant to 35 U.S.C. § 119(e), this application claims the benefit of Provisional Application No. 61/926,834 filed on Jan. 13, 2014, and this is a continuation-in-part of U.S. patent application Ser. No. 13/865,907 filed on Apr. 18, 2013, now U.S. Pat. No. 9,456,963, which claims the benefit of Provisional Application No. 61/738,970 filed on Dec. 18, 2012, the contents of which are all hereby incorporated by reference herein in their entirety.

FIELD OF INVENTION

The present invention relates to liquid type photo-curable resin compositions used for three-dimensional (3D) printing and a method for producing an artificial tooth or teeth and a denture base by a 3D printing process using the compositions. In particular, the present invention relates to dental compositions having low viscosity at a feeding temperature and a proper curing rate, low shrinkage, excellent biocompatibility, and superior mechanical properties. Such compositions are used in 3D printing to manufacture dentures having a distinctive denture base and a set of artificial teeth.

DESCRIPTION OF THE RELATED ART

In recent years, three-dimensional printing technologies have been used to produce a large number of items in a short period of time. There are several ways to build three-dimensional articles using photo-curable materials. One of the most efficient technologies for 3D printing is a digital light process (DLP) method or stereolithography (SLA). In a 3D printer using the DLP or SLA method, the photo-curable material, which is in a liquid form, is layered on a vat or spread on a sheet, and a predetermined area or surface of the photo-curable material is exposed to ultraviolet-visible (UV/Vis) light that is controlled by a digital micro-mirror device or rotating mirror. In the DLP method, additional layers are repeatedly or continuously laid and each layer is cured until a desired 3D article is formed. The SLA method is different from the DLP method in that the liquid material is solidified by a line of radiation beam. Even for the 3D printer using a multi-jetting method, the material is also in the liquid form at time of jetting. Therefore, most photo-curable resins for 3D printing methods are in the liquid form, having low viscosity and a curing rate that are proper for 3D printers.

An inkjet printing system may be used to load and print several materials at once. The resolution of the inkjet printing system is controlled by a nozzle size and the material should have viscosity that is sufficiently low to pass through the nozzle and to allow rapid curing before a new layer is spread on top of the cured layer. In contrast, the resolution of the digital light process method generally depends on the viscosity of photo-curable materials and can be controlled by a thickness of layers formed. In addition, the digital light process method requires a support bar instead of a support material required in the inkjet printing method such that the number of loading materials is limited to only one material. For example, U.S. Pat. Nos. 7,183,335 and 7,300,619 disclose a composition for use in inkjet type three dimensional printing. According to the printing method disclosed in these patent documents, several materials can be loaded together and a high resolution may be achieved in minimum operation time. However, most compositions for inkjet type printing disclosed in these patent documents are comprised of acrylate type components which are not suitable for use in dentures.

Conventional dental compositions or mixtures react slowly and have high viscosity. For example, (meth)acrylate materials, such as methyl methacrylate (MMA) and ethyl methacrylate, and high molecular weight poly(methyl methacrylate) (PMMA) have been used as materials for manufacturing artificial teeth and denture base resin because they are cheap and have good transparency, excellent moldability, and good physical properties. In general, the MMA monomer has slower reactivity than an acrylate monomer and has characteristic odor while when the high molecular weight PMMA or copolymer of PMMA is mixed with MMA, the mixture is in a putty state and curing takes long time. Therefore, conventional dental compositions cannot be applied to a 3D printing method because of their slow reactivity and putty state.

Thus, there is a need for simple and easily photo-curable liquid resin compositions that are formulated to be suitable for construction of denture bases and artificial teeth using a 3D printing method. Preferably, photo-curable liquid resin compositions to be used in the 3D printing have low viscosity, a proper curing rate, minimum shrinkage, and excellent mechanical properties.

SUMMARY OF THE INVENTION

Photo-curable liquid compositions and three-dimensional printing technology are provided. The photo-curable liquid compositions may be used for manufacturing artificial teeth and denture base. The inventive compositions have suitable viscosity and curing rate for three-dimensional printing, providing appropriate mechanical properties desired for denture base and artificial teeth. The inventive compositions also allow effective operation time for manufacturing dentures.

According to one exemplary embodiment of the present invention, a composition includes a light-curable viscous mixture that includes 0-50% by weight of a poly(methyl methacrylate)/methyl methacrylate; 5-20% by weight of at least one kind of multifunctional aliphatic (meth)acrylate; 5-40% by weight of at least one kind of aliphatic urethane (meth)acrylate oligomer; 25-65% by weight of at least one kind of difunctional bisphenol-A dimethacrylate; 0.1 to 5% by weight of at least one kind of a photoinitiator; 0.05 to 2% by weight of at least one kind of light stabilizer; and 0.1 to 3% by weight of color pigment based on the total weight of the composition.

According to another exemplary embodiment of the present invention, a composition includes a light-curable viscous mixture that includes 0-25% by weight of a poly(methyl methacrylate)/methyl methacrylate; 5-15% by weight of at least one kind of multifunctional aliphatic(meth)acrylate; 5-35% by weight of at least one kind of aliphatic urethane (meth)acrylate oligomer; 30-60% by weight of at least one kind of difunctional bisphenol-A dimethacrylate; 0.1 to 3.5% by weight of at least one kind of a photoinitiator; 0.05 to 1% by weight of at least one kind of light stabilizer; and 0.1 to 2% by weight of color pigment based on the total weight of the composition.

According to yet another exemplary embodiment of the present invention, a method of printing a denture using a composition including a light-curable viscous mixture, wherein the light-curable viscous mixture includes poly (methyl methacrylate)/methyl methacrylate solution, multi-functional methacrylate, urethane dimethacrylate, difunctional bisphenol-A dimethacrylate, a light-photopolymerization initiator, a colorant, and at least one type of stabilizer, includes stacking layers of the light curable mixture; and curing the stacked layers one-by-one using a three-dimensional printer.

DETAILED DESCRIPTION

The present invention relates to photo-curable compositions used to produce artificial teeth and denture base using a 3D printing system. In general, a photo-curable liquid resin composition according to an embodiment of the present invention includes a poly(methyl methacrylate) polymer having a high molecular weight and other methacrylate components to provide low viscosity with a curing rate proper for fabricating at least a denture base or artificial teeth using a 3D printing technology.

To prepare a solution miscible with a monomeric and oligomeric (meth)acrylate mixture and providing good mechanical properties, a high molecular weight poly(methyl methacrylate) polymer is dissolved into methyl methacrylate monomer. The molecular weight of the poly(methyl methacrylate) polymer may be from about 10,000 g/mol to about 400,000 g/mol. The amount of poly(methyl methacrylate) in the methyl methacrylate monomer may be from about 15 to about 45 wt %. If the molecular weight of the poly(methyl methacrylate) is less than 10,000 g/mol, mechanical properties of the cured product may be poor. If the molecular weight of the poly(methyl methacrylate) is greater than 400,000 g/mol, the amount of the poly(methyl methacrylate) in the methyl methacrylate monomer solution should be greater than 15%. Otherwise the mechanical properties of the cured product may be poor. If more than 40 wt % of poly(methyl methacrylate) having greater than 400,000 g/mol is added into the monomer, it may be too hard to handle because such a mixture would be too viscous. Further, since the poly(methyl methacrylate) polymer may not dissolve well in other components, the poly(methyl methacrylate) polymer must be dissolved in the methyl methacrylate monomer first and then, the dissolved poly(methyl methacrylate) polymer may be further mixed with other components in order to make a homogenous mixture.

In the conventional composition used for preparation of a denture base, a powder- or bead-type PMMA polymer is mixed with methyl methacrylate monomer and the ratio between the powder and the monomer liquid is about 2:1. Once a mixture is generated, the mixture is in a paste-like state or becomes a very thick viscous material. Since it is difficult to use a material in a putty or paste-like state in a 3D printing system, the conventional composition, i.e., the above-described mixture of the PMMA polymer and methyl methacrylate monomer, may not be used in 3D printing. Therefore, the PMMA polymer must be first dissolved into the monomer to be in a liquid state.

The viscosity of the PMMA/MMA solution is less than 10000 centipoise (cps) at room temperature. Optionally, multi-functionalized methacrylate diluent (B) having low viscosity may be first added into the poly(methyl methacrylate)/methyl methacrylate solution to make a low viscosity mixture.

In one example embodiment of the present invention, any type of methacrylates having a functionality of two or more can be employed as a component in the composition used for preparation of a denture base and artificial teeth. The polyfunctional monomer serves to enhance the curing rate, adjust viscosity, and improve toughness and adhesion between the artificial teeth and the denture base.

Examples of the multifunctional monomeric methacrylates include ethylene glycol dimethacrylate, diethylene glycol dimethacrylate, triethylene glycol dimethacrylate, polyethylene glycol dimethacrylate, 2,2 bis[4-(methacryloxy ethoxy)phenyl]propane, tricylodecane dimethanol dimethacrylate, 1,10-decandiol dimethacrylate, 1,6-hexanediol dimethacyrlate, 1,9-nonanediol dimethacrylate, neopentyl glycol dimethacrylate, 2-hydroxy 1-3 dimethacryloxy proane, trimethyolpropane trimethacrylate, ethoxylated trimethyol propane trimethacrylate, ditrimethyolpropane tetramethacrylate, tris (2-hydroxy ethyl) isocyanurate trimethacrylate, dipentaerythritol pentamethacrylate, ethyoxylated pentaerythritol tetramethacrylate, propoxylated glyceryl trimethacrylate, propoxylated trimethylolpropane trimethacrylate, and polyester dendrimer. These compounds are known and commercially available.

In one example embodiment of the present invention, the urethane(meth)acrylate as component (C) can be prepared in a known manner, for example, by reacting a diisocyanate with a polyester or polyether polyol to yield an isocyanate terminated urethane followed by reacting with a hydroxyl terminated (meth)acrylates. The acrylation provides unsaturation or the (C=C) groups of the oligomer. The urethane (meth)acrylate further includes aliphatic or aromatic urethane acrylates and the aliphatic or aromatic chain may be linked by ether or ester groups or combination thereof.

Urethane(meth)acrylates are also available commercially under the trade name PHOTOMER from Cognis, GENOMER from Rahn, DOUBLEMER from Double Bond Chemical Inc., and CN1963, CN1964 from Sartomer Company.

As difunctional bisphenol A dimethacrylate (D), also known as monomeric bisphenol-A dimethacrylate having a bifunctionality, which provides excellent mechanical properties, a high glass transition temperature, and a fast curing rate, may be used in the above-identified compositions used for preparation of the denture base and artificial tooth. It is to be understood that the term "bisphenol-A" is commonly used in the art to indicate chemical compound 2,2-bis(4-hydroxyphenyl)propane.

One of most popular crosslinking dental dimethacrylates is 'bis-GMA' developed by R. L. Bowen about 40 years ago. It is also to be understood that the term "bis-GMA" is commonly used to indicate chemical compound 2,2-bis(4-(2-hydroxy-3-methacryloxypropoxy)-phenyl) propane, otherwise, referred to as "digycidyl methacrylate ester of bisphenol-A" or "bisphenol-A digycidyl ether" in the dental field.

Bis-GMA type dimethacrylate is superior to other dimethacrylates because of its relatively high molecular weight and stiffness, partially aromatic molecular structure, low polymerization shrinkage, rapid hardening, low volatility, high refractive index, good adhesion property, and excellent mechanical properties of cured resins. Examples of bisphenol A dimethacrylate include ethoxylated bisphenol A dimethacrylate having ethoxy groups (2 moles to 10 moles) and hydrogenated bisphenol A dimethacrylate.

Compounds such as bisphenol A dimethacrylate are known and are commercially available. For example, Sartomer company provides such compounds under product names SR348, SR540, SR542, SR480, and SR541. Other companies such as Rahn provide such compounds under the trade names MIRAMER and GENOMER and Cognis also provides such compounds under the trade name PHOTOMER.

A composition according to an embodiment of the present invention includes a photoinitiator (E) which functions to generate radicals by UV/Vis light to initiate crosslinking of unsaturated hydrocarbons. Representative examples of the photoinitiator include bis(2,4,6-trimethyl benzoyl)phenyl phosphine oxide (IRGACURE 819), 2,4,6-trimethylbenzoyl diphenyl phosphine (TPO), 2-hydroxy-2-methyl-1-phenyl-1-propane (DAROCUR 1173), benzophenone (BP) and the like, and it is used in an amount ranging from 0.

According to another embodiment of the present invention, the composition may also include one or more stabilizers (F). Suitable stabilizers include, but are not limited to, 4-methoxyphenol, butylated hyrdorxytoluene (2,6-di-t-butyl-4-methylphenol), phenothiazine, bistridecylthiodipropionate, and hinder amines.

According to yet another embodiment of the present invention, the composition optionally may include a pigment composition including a pigment or combination of pigments to provide desired colors. A combination of pigments and dyes may also be used. For example, the amount of the combination of pigments may be less than 3% by weight, preferably less than 2% by weight, based on the total weight of the composition.

According to yet another embodiment of the present invention, the composition may contain inorganic fillers. Examples of inorganic filler material include fused silica, synthetic silica, alumina silicate, amorphous silica, glass ceramic, soda glass, lithium borosilicate glass, barium glass, strontium glass, zinc glass, fluoroaluminum borosilicate glass, borosilicate glass, crystal quartz, and a mixture thereof. The inorganic filler particle may include silica particles having an average diameter of less than about 300 nm, preferably less than about 200 nm. The silica particles used in the composition are preferably substantially spherical and substantially non-porous.

Moreover, the inorganic filler including silica-based fine particles and coatings of an oxide that cover surfaces of the silica-based fine-particles may be used in the composition. The oxide may contain a zirconium atom, a silicon atom, and an oxygen atom to provide excellent transparency.

Suitable nano-sized silicas are commercially available from DeGussa AG, (Hanau, Germany) under product name AEROSIL OX-50, -130, -150, and -200 or from Cabot Corp (Tuscola, Ill.) under product name CAB-O-SIL M5.

In the filler, the oxide coating layers of fine particles may be functionalized using reactive components and this functionalization of the fine particles is called surface-modification or surface-treatment. The surface-modification or surface-treatment provides reactivity to fillers that participate in a chemical reaction and/or homogenous dispersion in a compounding system. Surface-modified nano-sized silica particles provide stable dispersion in the solution before the composition is used since the particles do not aggregate and are not settled after standing for a certain period of time at room temperature. The surface-modified particles are well dispersed in the photo-curable composition, and thus, help achieving a substantially homogenous composition.

The surface-modified silica particles according to an example embodiment of the present invention are preferably treated with a resin-compatibilizing surface treatment agent. For example, preferred surface treatment or surface modifying agents include silane treatment agents.

When a surface of the silica particle is modified or coated with the silane treatment agents having functional groups such as acryl group or methacryl group that can participate in the polymerization reaction in a methacrylate composition, the silica particle is referred to as functionalized silane-treated particles. If the surface of silica particle is not modified or coated, the silica particle is referred to as unfunctionalized silane-treated silica.

Examples of the surface modifying silane agents include methyltrimethoxysilane, dimethyldimethoxysilane, phenyltrimethoxysilane, diphenyldimethoxysilane, methyltriethoxysilane, diemthyldiethoxysilane, vinyltrimethoxysilane, vinyltriethoxysilane, methyldicrholorsilane, dimethyldichlorosilane, trimethylchlorosilane, vinyltrichlorosilane, trimethylbromosilane, diethylsilane, and similar agents.

Among these, a surface modifying agent having functional group which can be reacted in the polymerization during curing may include, for example, ω-methacryloxyalkyl trimethoxysilane having 3 to 15 carbon atoms between a methacryloxy group and a silicon atom, ω-methacryloxyalkyl triethoxysilane having 3 to 15 carbon atoms between a methacryloxy group and a silicon atom, vinyltrimethoxysilane, vinyltriethoxysilane, vinyltriacetoxysilane, and γ-glycidoxypropyltrimethoxysilane. More preferable silane treatment agent includes 3-methacryloxylpropyltrimethoxysilane, 8-methacryloyloxyoctyltrimethoxysilane, 9-methacryloyloxynonyltrimethoxysilane, 10-methacryloyloxydecyltrimethoxysilane, 11-methacryloyloxyundecyltrimethoxysilane, 11-methacryloyloxyundecyldichloromethylsilane, and 11-methacryloyloxyundecyltrichlorosilane.

These surface modifying agents may be used alone, or as a combination of two or more thereof. These agents are available commercially under the trade name GENOSIL GF31 and XL33 and in particular, 3-glycidoxypropyltrimethoxy silane is available commercially under the trade name GENOSIL GF80 and GF82 from Wacker Chemie AG and AEROSIL R7200 from Evonik.

In another example embodiment of the present invention, the compositions may include, but are not limited to, a heavy metal oxide. For example, a suitable metal oxide may be an oxide of metals having an atomic number that is greater than 30 such as tungsten, bismuth, molybdenum, tin, zinc, cerium, yttrium, strontium, barium, zirconium, hafnium, niobium, tantalum, and a combination thereof.

The heavy metal oxide particles preferably have an average diameter of less than about 100 nm, more preferably less than about 70 nm, most preferably less than about 60 nm. Sometimes the heavy metal oxide can be aggregated and the aggregated particles should be less than about 200 nm, preferably less than about 100 nm in average diameter.

In one embodiment of the present invention, the composition optionally may include a surface tension reducing agent to provide lower surface tension by lowering surface energy, better wetting. Examples of surface tension reducing agents are silicone surface additives, marketed by Byk Chemie under the trade name BYK or marketed by Dow Corning under the trade name DOW CORNING series.

EXAMPLES

1. Preparation of Poly(Methyl Methacrylate)/Methyl Methacrylate Monomer Premixture The bead or powder type PMMA was added to the MMA solvent in a ratio of 1:2. Two PMMAs having different molecular weights were used. Table 1 shows the materials used in PMMA/MMA solutions. A mixture of two different PMMAs may be used.

TABLE 1

| Type | Materials | Molecular weight (g/mol) | Manufacturer |
|---|---|---|---|
| Bead | Poly (methyl methacrylate) | 110,000 | LGMMA |
| Bead | Poly (methyl methacrylate) | 300,000 | Sigma-Aldrich |
| Liquid | Methyl methacrylate | 100 | Sigma-Aldrich |

The mixture was initially cloudy due to dispersed PMMA powder or beads. However, the mixture turned to a clear solution after overnight stirring. To prevent evaporation of the MMA, the mixture container was capped with a lid during the stirring at room temperature.

2. Preparation of the Mixture

A portion of the pre-mixture was taken from the PMMA/MMA solution. Components listed in Table 2 were added into the pre-mixture. Since the urethane dimethacrylate and bisphenol-A glycidyl methacrylate had high viscosities, the components were heated up in a 70° C. convention oven for 2-3 hours before being added to the mixture.

TABLE 2

| | Description | Trade Name | Manufacturer |
|---|---|---|---|
| Component a) | PMMA 110/MMA | — | Home-made |
| | PMMA 300/MMA | — | Home-made |
| Component b) | Trimethylolpropane trimethacrylate | SR350 | Sartomer |
| | Diethylene glycol dimethacrylate | SR231 | Sartomer |
| | 1,6-hexandiaol dimethacyrlate | SR239 | Sartomer |
| Component c) | Urethane dimethacrylate | CN1963 | Sartomer |
| | Urethane methacrylate | CN1964 | Sartomer |
| Component d) | Ethoxylated Bisphenol-A dimethacrylate | SR540 | Sartomer |
| | Bisphenol-A glycidyl methacrylate | X-950-0000 | Esstech, Inc. |
| Component e) | bis(2,4,6-trimethyl benzoyl)phenyl phosphine oxide | IRGACURE 819 | BASF |
| | 2,4,6-trimethylbenzoyl diphenyl phosphine | LUCIRIN TPO | BASF |
| Component f) | Stabilizer | 4-methoxyphenol | Sigma-Aldrich |
| Optional g) | Silane treated silica | AEROSIL R7200 | Evonik, Inc. |

TABLE 3

| Component | | 1 | 2 | 3 | 4 | 5 | 6 | 7 |
|---|---|---|---|---|---|---|---|---|
| Component a) | PMMA 110/MMA | X | X | X | X | X | | |
| | PMMA 300/MMA | | | | | | X | X |
| Component b) | SR350 | X | X | X | X | X | | |
| | SR231 | | | | | | X | |
| | SR239 | | | | | | | X |
| Component c) | CN1963 | X | X | X | X | | | |
| | CN1964 | | | | | X | X | X |
| Component d) | SR540 | X | X | X | X | X | | |
| | X-950-0000 | | | | | | X | X |
| Component e) | Irgacure 819 | X | X | X | X | X | | |
| | Lucirin TPO | | | | | | X | X |
| Component f) | 4-methoxyphenol | X | X | X | X | X | X | X |
| Component g) | Aerosil R7200 | | | X | X | X | | |

3. 3D Printing, Material Properties and Biocompatibility Tests

After preparation of the mixture, viscosities of the mixtures were measured at room temperature and at printing temperature. Curing time was adjusted based on the basic printing shape test to get the accurate shape. The curing times and measured viscosities of the mixtures 70° C. are listed in Table 4. In exemplary embodiments of the present invention, the viscosity of the composition is measured using a BROOKFIELD DV II+ Programmable Viscometer equipped with a proper spindle at 70° C. Before measuring the viscosity at 70° C., the composition was held for 3 hours in the oven which was set as 70° C. and then the viscosity was measured.

The specimens for flexural test were printed using CARIMA 3D printer (Seoul, S. Korea) at 70° C. and then post cured by a UV/Vis curing machine for 2 hours. Before measuring the flexural properties, the specimens were conditioned in 37° C. water for 50 hours. The flexural strength and modulus were measured at 37° C. in a warm bath. The test results are showed in Table 4.

TABLE 4

| Properties | Composition No. | | | | | | |
|---|---|---|---|---|---|---|---|
| | 1 | 2 | 3 | 4 | 5 | 6 | 7 |
| Viscosity (cps) at 70° C. | 120 | 174 | 351 | 464 | 310 | 618 | 532 |
| Curing time (sec) | 12 | 11 | 10 | 9 | 10 | 10 | 9 |
| Flexural strength (MPas) | 55.5 | 81.6 | 72.4 | 65.6 | 68.1 | 70.4 | 76.1 |
| Flexural modulus (MPas) | 1540 | 1870 | 2030 | 2270 | 2410 | 2360 | 2430 |

Further, samples of composition Nos. 1 and 2 were used to test cytotoxicity. Sample specimens (2×6×0.2 cm$^3$) for cytotoxicity test on composition Nos. 1 and 2 were printed using a 3D printer. After the printing, the specimens were removed from the printer, washed with isopropanol alcohol, dried, and post cured by a UV/Vis curing machine (UV honle) for 1 hr. Thereafter, sample specimens were cut into a size of 1×1×0.2 cm$^3$. The prepared samples (16 totals for each composition) were divided into two groups; one group conditioned in a dry state and the other group conditioned in an artificial saliva state. The prepared samples were stored in a dry condition or artificial saliva for 7 days and thereafter placed in a prepared lymphocyte cell culture. Viability of peripheral blood lymphocytes was evaluated at the time of placement in the cell culture and after 14 and 21 days using a dye exclusion technique by simultaneous staining with ethidium bromide and acridine orange. Quantitative assessments were made by determination of percentages of viable, apoptotic and necrotic cells. For statistical analysis, Pearson chi-square test was used. In the cytotoxicity test, redistilled water was used as a negative control. Table 5 shows the results of the cytotoxicity test.

TABLE 5

| Storage Condition | Composition | Percentage of cells ± S.D. | Time elapsed from setting | | |
|---|---|---|---|---|---|
| | | | 0 day | 7 days | 14 days |
| Dry | Composition 1 | Viable | 88.5 ± 0.7 | 93.0 ± 1.4 | 92.5 ± 0.8 |
| | | Apoptosis | 10.5 ± 2.1 | 7.0 ± 1.4 | 7.5 ± 0.7 |
| | | Necrosis | 1.0 ± 1.4 | 0.0 ± 0.0 | 0.0 ± 0.0 |
| | Composition 2 | Viable | 92.1 ± 0.7 | 96.0 ± 1.4 | 95.0 ± 0.8 |
| | | Apoptosis | 8.0 ± 1.4 | 4.0 ± 1.4 | 5.0 ± 0.7 |
| | | Necrosis | 0.0 ± 0.0 | 0.0 ± 0.0 | 0.0 ± 0.0 |
| Artificial saliva | Composition 1 | Viable | 96.5 ± 3.5 | 95.5 ± 2.1 | 94.0 ± 1.4 |
| | | Apoptosis | 3.5 ± 3.5 | 4.0 ± 1.4 | 6.0 ± 1.4 |
| | | Necrosis | 0.0 ± 0.0 | 0.5 ± 0.7 | 0.0 ± 0.0 |
| | Composition 2 | Viable | 94.5 ± 2.1 | 94.5 ± 0.7 | 96.5 ± 0.7 |
| | | Apoptosis | 5.5 ± 2.1 | 5.5 ± 0.7 | 3.5 ± 0.7 |
| | | Necrosis | 0.0 ± 0.0 | 0.0 ± 0.0 | 0.0 ± 0.0 |
| Negative control | Redistilled water | Viable | 95.5 ± 1.4 | 94.5 ± 2.1 | 94.5 ± 0.7 |
| | | Apoptosis | 5.0 ± 1.4 | 5.5 ± 2.1 | 5.5 ± 0.7 |
| | | Necrosis | 0.0 ± 0.0 | 0.0 ± 0.0 | 0.0 ± 0.0 |

For both composition 1 and composition 2 subjected to artificial saliva, the numbers of viable cells showed no statistical significant difference when compared to the negative control group (p<0.01). Thus, composition 1 and composition 2 showed excellent biocompatibility compared to the negative control group (redistilled water), and thus, a dental resin made of compositions 1 and 2 would be safe for clinical use.

4. Denture Preparation

Into the mixture, a pink pigment was added for a denture base and a white pigment was added for artificial teeth. Using CARIMA 3D printer, a 3D virtual denture base model and an artificial teeth model generated by Dentca (Los Angeles, Calif.) software were separately printed. The printed denture base and teeth were removed from the supports, washed with isopropanol alcohol and assembled by using dental adhesives. After the assembled denture was polished by a polishing unit, it was coated with dental coating materials by a spray coating method to provide gloss.

As discussed, the compositions disclosed herein are suitable for use in 3D printing of dentures. It will be apparent to those skilled in the art that various modifications and variations can be made in the example embodiments of the present invention without departing from the spirit or scope of the invention. Thus, it is intended that the present invention covers the modifications and variations of the example embodiments disclosed herein provided they come within the scope of the appended claims and their equivalents.

What is claimed is:

1. A composition comprising:
   a light-curable mixture comprising:
   0-50% by weight of a poly(methyl methacrylate)/methyl methacrylate;
   5-20% by weight of at least one kind of multifunctional aliphatic (meth)acrylate;
   5-40% by weight of at least one kind of aliphatic urethane (meth)acrylate oligomer;
   25-65% by weight of at least one kind of difunctional bisphenol-A methacrylate;
   0.1 to 5% by weight of at least one kind of a photoinitiator;
   0.05 to 2% by weight of at least one kind of light stabilizer; and
   0.1 to 3% by weight of color pigment based on the total weight of the composition, wherein viscosity of the composition is less than about 700 centipoise (cps) at 70° C. such that the composition is used in a three-dimensional printer, wherein flexural strength of specimens printed by the three-dimensional printer using the composition and post cured by a curing machine is greater than 50 MPa, wherein molecular weight of the poly(methyl methacrylate) is between about 10,000 to about 400,000 g/mol, and wherein the composition is used for manufacturing artificial teeth and dentures using the three-dimensional printer.

2. The composition of claim 1, wherein the viscosity of the composition is greater than about 100 centipoise (cps) at 70° C.

3. The composition of claim 1, wherein viscosity of the mixture of poly(methyl methacrylate)/methyl methacrylate is less than 10000 cps at 25° C.

4. The composition of claim 1, further comprising a light-photo-polymerization initiator, wherein the light-photo-polymerization initiator comprises acylphosphine oxide compounds.

5. A composition comprising:
a light-curable mixture comprising:
0-25% by weight of a poly(methyl methacrylate)/methyl methacrylate;
5-15% by weight of at least one kind of multifunctional aliphatic (meth)acrylate;
5-35% by weight of at least one kind of aliphatic urethane (meth)acrylate oligomer;
30-60% by weight of at least one kind of difunctional bisphenol-A methacrylate;
0.1 to 3.5% by weight of at least one kind of a photoinitiator;
0.05 to 1% by weight of at least one kind of light stabilizer; and
0.1 to 2% by weight of color pigment based on the total weight of the composition,
wherein viscosity of the composition is less than about 700 centipoise (cps) at 70° C. such that the composition is used in a three-dimensional printer,
wherein flexural strength of specimens printed by the three-dimensional printer using the composition and post cured by a curing machine is greater than 50 MPa,
wherein molecular weight of the poly(methyl methacrylate) is between about 10,000 to about 400,000 g/mol, and
wherein the composition is used for manufacturing artificial teeth and dentures using the three-dimensional printer.

6. The composition of claim 5, wherein the viscosity of the composition is greater than about 100 centipoise (cps) at 70° C.

7. The composition of claim 5, further comprising 2.5-12% by weight of at least one kind of surface modified silica-based fine particles.

8. The composition of claim 7, wherein the surface modified silica-based fine particles comprise non-reactive and reactive silica particles that are surface-modified by a surface modifying agent.

9. The composition of claim 8, wherein the surface modifying agent comprises compounds containing methacryloxy groups.

10. The composition of claim 7, wherein the surface modified silica-based fine particles have an average particle size that is less than 200 nm.

11. A method of printing a denture using the composition of claim 1, the method comprising:
stacking layers of the light curable mixture; and
curing the stacked layers one-by-one using the three-dimensional printer based on Computer-Aided Design/Computer-Aided Manufacturing (CAD/CAM) generated information that is related to the denture to be manufactured.

12. The method of claim 11, wherein the three-dimensional printer is operated according to a digital light processing method or a stereolithography method.

13. The method of claim 11, wherein:
the stacked layers are cured based on computer generated information that is related to the denture; and
the information comprises a digital model generated based on a dental impression of a patient's mouth and a Computer-Aided Design/Computer-Aided Manufacturing (CAD/CAM) design.

14. The method of claim 11, wherein the denture comprises a printed denture base portion and a printed artificial teeth portion formed as a single body.

15. The method of claim 11, further comprising assembling the denture base and the artificial teeth with dental adhesives after printing the denture base and the artificial teeth separately.

16. The method of claim 11, wherein the denture comprises a partial denture and a full denture.

17. A method of printing a denture using the composition of claim 5, the method comprising:
stacking layers of the light curable mixture; and
curing the stacked layers one-by-one using the three-dimensional printer based on Computer-Aided Design/Computer-Aided Manufacturing (CAD/CAM) generated information that is related to the denture to be manufactured.

18. The composition of claim 1, wherein flexural modulus of the composition is between about 1500 Mpas and 2450 Mpas.

19. A composition comprising:
a light-curable mixture comprising:
0-50% by weight of a poly(methyl methacrylate)/methyl methacrylate;
5-20% by weight of at least one kind of multifunctional aliphatic (meth)acrylate;
5-40% by weight of at least one kind of aliphatic urethane (meth)acrylate oligomer;
25-65% by weight of at least one kind of difunctional bisphenol-A methacrylate;
0.1 to 5% by weight of at least one kind of a photoinitiator;
0.05 to 2% by weight of at least one kind of light stabilizer; and
0.1 to 3% by weight of color pigment based on the total weight of the composition,
wherein viscosity of the composition is less than about 700 centipoise (cps) at 70° C. such that the composition is used in a three-dimensional printer,
wherein flexural strength of specimens printed by the three-dimensional printer using the composition and post cured by a curing machine is greater than 50 MPa,
wherein molecular weight of the poly(methyl methacrylate) is between about 10,000 to about 400,000 g/mol, and
wherein the viscosity of the composition is greater than about 100 centipoise (cps) at 70° C.

* * * * *